United States Patent [19]
Uchida et al.

[11] Patent Number: 4,723,025
[45] Date of Patent: Feb. 2, 1988

[54] UNSATURATED SILANE COMPOUNDS

[75] Inventors: Kingo Uchida, Ikeda; Akira Nagata, Osaka; June Iyoda, Ikeda, all of Japan

[73] Assignee: Agency of Industrial Science & Technology, Tokyo, Japan

[21] Appl. No.: 12,526

[22] Filed: Feb. 9, 1987

[30] Foreign Application Priority Data

Jun. 13, 1986 [JP] Japan ................................. 61-138956

[51] Int. Cl.$^4$ ................................................ C07F 7/08
[52] U.S. Cl. ........................................................ 556/440
[58] Field of Search ......................................... 556/440

[56] References Cited

U.S. PATENT DOCUMENTS

| | | | |
|---|---|---|---|
| 2,922,806 | 1/1960 | Merker | 556/440 |
| 2,956,044 | 10/1960 | Merker | 556/440 X |
| 3,317,369 | 5/1967 | Clark et al. | 556/440 X |
| 3,324,074 | 6/1967 | McManimie | 556/440 X |
| 3,377,371 | 4/1968 | Quaal | 556/440 |
| 3,700,714 | 10/1972 | Hamilton et al. | 556/440 |
| 3,746,734 | 7/1973 | Berger et al. | 556/440 |

FOREIGN PATENT DOCUMENTS 42-23332 of 1967 Japan ................................. 556/440

Primary Examiner—Paul F. Shaver
Attorney, Agent, or Firm—Armstrong, Nikaido, Marmelstein & Kubovcik

[57] ABSTRACT

Disclosed are new unsaturated silane compounds of the following general formula:

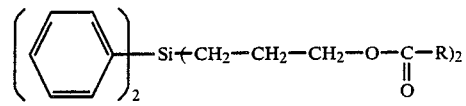

wherein R represents a vinyl, 1-methylvinyl or allyloxy group.

4 Claims, No Drawings

UNSATURATED SILANE COMPOUNDS

BACKGROUND OF THE INVENTION

The present invention relates to new unsaturated silane compounds. More particularly, the invention relates to radical-polymerizable monomers capable of forming a three-dimensional polymer having excellent transparency, high refractive index and high heat resistance.

As optical plastic materials, poly(methyl methacrylate), polycarbonates and diethylene glycol bisallyl carbonate (CR-39) have been known.

However, poly(methyl methacrylate) and polycarbonates cannot be cut or polished easily, since they are linear, thermoplastic polymers.

The CR-39 resin has a defect that its refractive index is as low as 1.500 and, therefore, when it is used as a material for a lens, the thickness of center and edge of the formed lens are inevitably increased.

On the contrary, polymers containing silicon have generally high heat resistance and transparency.

The inventors prepared a silicon-containing polymerizable monomers having an aromatic ring and usable as a component for increasing the refractive index of resins, and found that this monomer is a new compound and the resins that have these monomers as a component have high refractive indices, transparency and heat resistance and suitable for use as an optical material for lenses and prisms. The present invention has been completed on the basis of these findings.

SUMMARY OF THE INVENTION

A first object of the present invention is to provide new unsaturated compounds containing silane.

A second object of the invention is to provide monomers capable of forming a polymer having high refractive index and transparency and suitable for use as optical plastic materials.

THE PREFERRED EMBODIMENTS

The new silane compounds of the present invention are represented by the following general formula:

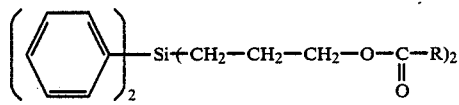

wherein R represents a vinyl, 1-methylvinyl or allyloxy group.

Examples of the structures of the new unsaturated silane compounds of the present invention include the following ones:

bis(3-acryloyloxypropyl)diphenylsilane: (1)

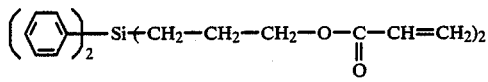

bis(3-methacryloyloxypropyl)diphenylsilane: (2)

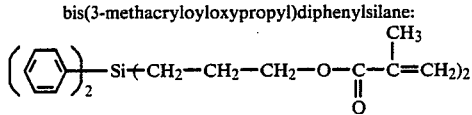

bis(3-allyloxycarbonyloxyproply)diphenylsilane: (3)

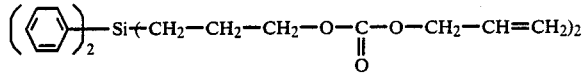

The new unsaturated silane compounds (D) of the present invention are prepared by reacting bis(3-hydroxypropyl)diphenylsilane (B) with a corresponding acid chloride (C) having a polymerizable group R in the presence of a dehydrochlorinating agent as shown by the following reaction formula:

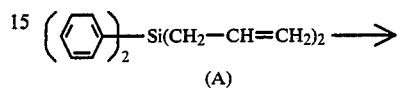

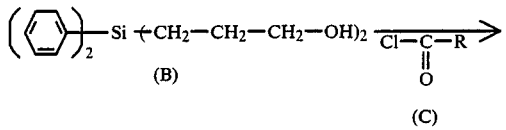

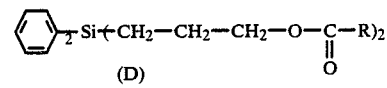

As the dehydrochlorinating agent, a base such as pyridine or triethylamine is used.

The compound (B) is prepared by hydroboration of commercially available diallyldiphenylsilane (A) with a borane/tetrahydrofuran solution, followed by oxidative degradation with $H_2O_2$.

In the above general formulae (C) and (D), R represents a vinyl, 1-methylvinyl or allyloxy group.

The unsaturated silane compounds (D) of the present invention are new compounds.

These compounds can be homo-polymerized or co-polymerized easily in the presence of a radical polymerization initiator such as benzoyl peroxide or diisopropyl peroxydicarbonate. The obtained homopolymers or copolymers of the new compounds of the present invention have high transparency and refractive indices.

These homopolymers and copolymers can be processed by, for example, cutting or polishing because they are three-dimensional, crosslinked polymers. They are thus suitable for use as optical plastics.

Further, they have a high heat resistance because they are three-dimensional, crosslinked polymers having a phenyl-silicon bond.

The following examples will further illustrate the present invention.

EXAMPLE 1

Preparation of bis(3-acryloyloxypropyl)diphenylsilane (D-1) (dehydrochlorinating agent: triethylamine)

60 ml of tetrahydrofuran (THF) was placed in a flask purged with argon gas. 70 ml of 1M borane-THF solution was added thereto under stirring while the latter was kept at 0° C.

A solution of 22.5 g (85.1 mmol) of diallyldiphenylsilane (A) in 30 ml of THF was added dropwise thereto in 20 min.

After completion of the addition, the temperature was raised to room temperature and stirring was continued for 3 h. The mixture was then heated to 40° C. for 30 min.

10 ml of water, 40 ml of a 3N aqueous sodium hydroxide solution and 25 ml of a 30% aqueous hydrogen peroxide solution were added successively thereto while the flask was cooled externally in a water bath.

After completion of the reaction, the reaction mixture was diluted with water and extracted with ether. The extract was dried over magnesium sulfate. The solvent was distilled off to obtain 24.2 g (yield: 94.8%) of bis(3-hydroxypropyl)diphenylsilane (B) (m.p. 80°-81° C.).

The structure of the obtained product was identified from the fact that the determined spectral data thereof coincided with those mentioned in literature [R. A. Felix, W. P. Webber, J. Org. Chem., 37, 2323 (1972)].

Then, 400 ml of dry benzene was placed in a flask purged with an inert gas (argon). 10.0 g (33.3 mmol) of the compound (B) and 7.7 g (77.0 mmol) of triethylamine as the dehydrochlorinating agent were dissolved therein.

30 ml of a solution of 6.6 g (73.3 mmol) of acryloyl chloride (C-1) in benzene was added dropwise to the solution.

After completion of the addition followed by stirring at 40° C. for 1 h, the reaction mixture was washed with a 0.5N hydrochloric acid solution, water, a 1N sodium carbonate solution and water successively and dried over magnesium sulfate.

Benzene was distilled off and the residue was purified according to column chromatography (silica gel/benzene).

7.7 g (18.9 mmol) of bis(3-acryloyloxypropyl)diphenylsilane (D-1) was obtained in the form of a colorless, transparent oil (yield: 56.9%).

The elementary analysis data, characteristic infrared absorption and NMR spectral data of the product are shown in Table 1.

EXAMPLE 2

Preparation of bis(3-acryloyloxypropyl)diphenylsilane (D-1) (dehydrochlorinating agent: pyridine)

4.53 g (15.1 mmol) of bis(3-hydroxypropyl)diphenylsilane (B) prepared in Example 1 and 2.7 g (35.9 mmol) of pyridine were dissolved in 250 ml of dry benzene. 20 ml of a solution of 3.14 g (34.7 mmol) of acryloyl chloride (C-1) in benzene was added dropwise to the solution in an argon gas atmosphere.

After completion of the addition followed by extraction effected in the same manner as in Example 1 and purification according to column chromatography (silica gel/benzene), 2.68 g (6.6 mmol) of compound (D-1) was obtained (yield: 43.4%).

EXAMPLE 3

Preparation of bis(3-methacryloyloxypropyl)diphenylsilane (D-2)

5.10 g (17 mmol) of the compound (B) and 3.2 g (41 mmol) of pyridine were dissolved in 300 ml of dry benzene. 4.2 g (40 mmol) of methacryloyl chloride (C-2) was added dropwise thereto in an argon atmosphere. After completion of the addition, the reaction was carried out at 40° to 50° C. for 3 h. Pyridine hydrochloride thus precipitated was filtered off and the filtrate (benzene solution) was treated in the same manner as in Example 2 and then purified according to column chromatography (silica gel/benzene) to obtain 6.2 g (14.2 mmol) of bis(3-methacryloyloxypropyl)diphenylsilane (D-2) in the form of a colorless, transparent oil (yield: 83.6% based on B).

The elementary analysis data, characteristic infrared absorption and NMR spectral data of the product are shown in Table 1.

EXAMPLE 4

Preparation of bis(3-allyloxycarbonyloxypropyl)diphenylsilane (D-3)

6.01 g (20 mmol) of the compound (B) and 3.8 g (40.8 mmol) of pyridine were dissolved in 150 ml of dry benzene. 4.6 g (44 mmol) of allyl chloroformate (C-3) was added dropwise to the solution in an argon atmosphere.

After completion of the addition, the mixture was left to stand at room temperature for 18 h and then heated at 40°to 50° C. for 5 h to complete the reaction.

The reaction mixture was cooled to room temperature and pyridine hydrochloride thus precipitated was filtered off. The filtrate was subjected to the same aftertreatment as in Example 1 and then purified according to column chromatography (silica gel/benzene) to obtain 8.61 g (18.4 mol) of bis(3-allyloxycarbonyloxypropyl)dihenylsilane (D-3) in the form of a colorless, transparent oil (yield: 92.0%).

The elementary analysis data, characteristic infrared absorption and NMR spectral data of the product are shown in Table 1.

TABLE 1

(D-1)

Elementary analysis: Found: C 70.23%, H 6.88%. Calculated for $C_{24}H_{28}SiO_4$: C 70.55%, H 6.91%.

IR (NaCl) cm$^{-1}$ 1725 (C=O), 1630 (C=$CH_2$), 1620 (C=$CH_2$), 1430 (Si—Ph), 1410, 1190, 1110, 980, 810, 730, 700.

$^1$H—NMR (CDCl$_3$) ppm 1.0-1.1 (4H, m, Si—CH$_2$—), 1.6-1.7 (4H, m, —CH$_2$—), 4.02 (4H, t, J=6.7 Hz, O—CH$_2$—), 5.68 (2H, dd, J=10.2, 1.8 Hz), 6.01 (2H, dd, J=17.5, 10.2 Hz), 6.72 (2H, dd, J=17.5, 1.8 Hz), 7.2-7.4 (10H, m, aromatic protons).

$^{13}$C—NMR (CDCl$_3$) ppm 166.1, 134.9, 134.8, 130.3, 129.5, 128.0, 127.9, 66.8, 23.2, 8.7.

(D-2)

Elementary analysis: Found: C 71.60%, H 7.28%. Calculated for $C_{26}H_{32}SiO_4$: C 71.52%, H 7.39%

IR (NaCl) 2920, 1715 (C=O), 1635 (C=$CH_2$), 1425 (Si—Ph), 1320, 1295, 1160, 1110, 1035, 935.

$^1$H—NMR (CDCl$_3$) ppm 1.1-1.2 (4H, m, Si—CH$_2$—), 1.6-1.8 (4H, m, —CH$_2$—), 1.92 (6H, dd, J=1.6, 0.9 Hz, CH$_3$), 4.11 (4H, t, J=7 Hz, O—CH$_2$—), 5.54 (2H, dd, J=1.6, 1.2 Hz), 6.08 (2H, dd, J=1.2, 0.9 Hz), 7.3-7.5 (10H, m, aromatic protons).

$^{13}$C—NMR (CDCl$_3$) ppm 167.3, 136.5, 134.8, 129.5, 128.0, 125.2, 66.9, 23.1, 18.3, 8.6.

(D-3)

Elementary analysis: Found: C 66.89%, H 6.67%. Calculated for $C_{26}H_{32}SiO_6$: C 66.64%, H 6.88%.

IR (NaCl) 1750 (C=O), 1650 (C=$CH_2$), 1430 (Si—Ph), 1400, 1365, 1260, 1110, 965, 795, 740, 705, 680.

$^1$H—NMR (CDCl$_3$) ppm 1.1-1.2 (4H, m, Si—CH$_2$—), 1.6-1.8 (4H, m, —CH$_2$—), 4.10 (4H, t, J=7 Hz, O—CH$_2$—), 4.61 (4H, ddd, J=7, 1.5, 1 Hz, —CH$_2$—CH=CH$_2$), 5.25 (2H, ddd, J=11, 1.5, 1.3 Hz, CH), 5.35 (2H, ddd, J=17, 1.3, 1 Hz, CH), 5.93 (2H, ddt, J=17, 11, 7 Hz, CH), 7.3-7.6 (10H, m, aromatic protons).

$^{13}C$—NMR (CDCl$_3$) ppm 154.9, 134.7, 131.7, 129.4, 127.9, 118.5, 70.1, 68.1, 23.1, 8.9.

We claim:

1. New unsaturated silane compounds of the following general formula:

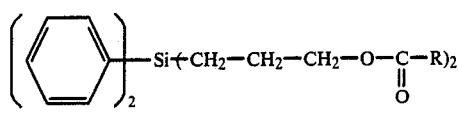

wherein R represents a vinyl, 1-methylvinyl or allyloxy group.

2. A new unsaturated silane compound according to claim 1, which is bis(3-acryloyloxypropyl)diphenylsilane.

3. A new unsaturated silane compound according to claim 1, which is bis(3-methacryloyloxypropyl)diphenylsilane.

4. A new unsaturated silane compound according to claim 1, which is bis(3-allyloxycarbonyloxypropyl)diphenylsilane.